(12) United States Patent
Cosmescu

(10) Patent No.: US 9,687,292 B2
(45) Date of Patent: Jun. 27, 2017

(54) ELECTROSURGERY HANDPIECE/PENCIL WITH SMOKE EVACUATION

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

(*) Notice: Subject to any disclaimer, the term of this patent is extended or adjusted under 35 U.S.C. 154(b) by 11 days.

(21) Appl. No.: 14/726,553

(22) Filed: May 31, 2015

(65) Prior Publication Data

US 2016/0346032 A1   Dec. 1, 2016

(51) Int. Cl.
*A61B 18/14* (2006.01)
*A61B 18/00* (2006.01)

(52) U.S. Cl.
CPC .. *A61B 18/1402* (2013.01); *A61B 2018/0094* (2013.01); *A61B 2018/00178* (2013.01); *A61B 2018/00589* (2013.01); *A61B 2018/00601* (2013.01); *A61B 2018/00607* (2013.01); *A61B 2018/00922* (2013.01); *A61B 2218/008* (2013.01)

(58) Field of Classification Search
CPC .............. A61B 18/1477; A61B 18/042; A61B 2018/00607; A61B 2018/00916; A61B 2018/00922; A61B 2018/00958; A61B 2018/1425; A61B 2018/1427; A61B 2018/1472; A61B 2018/1475; A61B 2018/1412

USPC ................. 606/37, 41, 42; 607/99, 115, 116
See application file for complete search history.

(56) References Cited

U.S. PATENT DOCUMENTS

| | | | | |
|---|---|---|---|---|
| 3,911,241 A | * | 10/1975 | Jarrard | A61B 18/1402 200/302.2 |
| 5,256,138 A | * | 10/1993 | Burek | A61B 18/042 606/42 |
| 8,672,937 B2 | * | 3/2014 | DeCarlo | A61B 18/1477 606/31 |
| 2014/0052131 A1 | | 2/2014 | Busch-Madsen et al. | |
| 2014/0142568 A1 | * | 5/2014 | Bernard | A61B 18/1402 606/37 |
| 2014/0257273 A1 | | 9/2014 | Cosmescu | |

FOREIGN PATENT DOCUMENTS

WO   2015/039232 A1   3/2015

* cited by examiner

*Primary Examiner* — Thomas Giuliani
(74) *Attorney, Agent, or Firm* — Zeman-Mullen & Ford, LLP

(57) ABSTRACT

An electrosurgery handpiece/pencil with smoke evacuation having features that support use at high frequencies without insulation breakdown and that provides increased efficiency of smoke evacuation during cutting and/or coagulation. The electrosurgery handpiece/pencil with smoke evacuation includes a circuit board contained within a heat shrinkable plastic sleeve that is seated on a planar platform.

23 Claims, 7 Drawing Sheets

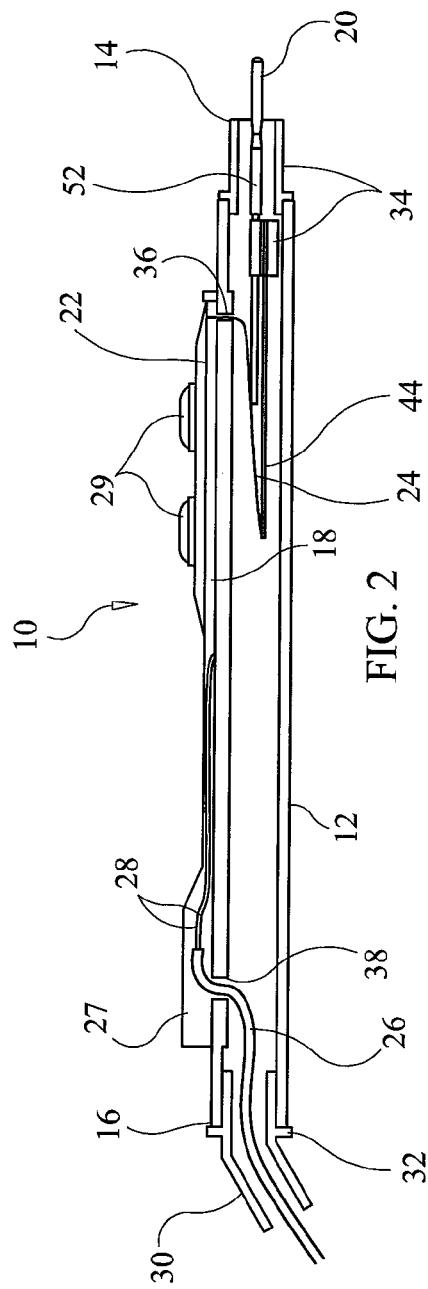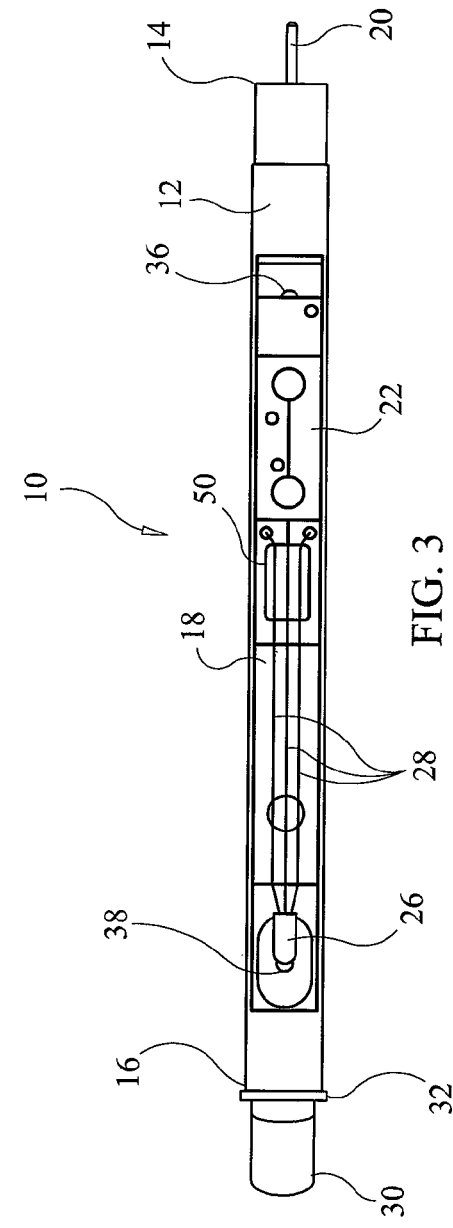

ELECTROSURGERY HANDPIECE/PENCIL WITH SMOKE EVACUATION

FIELD OF INVENTION

The present invention is generally directed to an electrosurgery handpiece/pencil, and more specifically to an electrosurgery handpiece/pencil with smoke evacuation that is constructed and designed to support its use at a high frequency rating without insulation breakdown. The electrosurgery handpiece/pencil with smoke evacuation of the present invention is also constructed and designed to provide maximum smoke evacuation during cutting and/or coagulation when using the electrosurgery handpiece/pencil.

BACKGROUND OF THE INVENTION

Electrosurgery handpieces/pencils that perform cutting and/or coagulation while simultaneously evacuating smoke and/or debris from the surgical site are well known in the art including electrosurgery handpieces/pencils with smoke evacuation that have telescopic members which enable a user to extend the length of the handpiece/pencil.

The present invention is directed to an electrosurgery pencil/handpiece with smoke evacuation having a streamlined design and construction which includes improved features and elements that enable use of the electrosurgery handpiece/pencil at high frequencies without insulation breakdown and maximum smoke evacuation during cutting and/or coagulation. The electrosurgery handpiece/pencil with smoke evacuation of the present invention provides increased protection to a user/surgeon and patient during use of the electrosurgery handpiece/pencil and enhanced efficiency for smoke evacuation during use of the electrosurgery handpiece/pencil.

SUMMARY OF THE INVENTION

The present invention is directed to an electrosurgery handpiece/pencil with smoke evacuation that includes a hollow tubular handpiece member having a first end and a second end, a planar platform located near a top of the hollow tubular handpiece member, an electrode positioned within the first end of the hollow tubular handpiece member, a circuit board seated on the planar platform where the circuit board is contained within a heat shrinkable plastic sleeve that has been heat shrunk to conform to the circuit board, at least one wire for connecting the circuit board to the electrode, an electrical cord containing one or more insulated wires for connecting the circuit board to an energy source, and one or more depressable button members positioned above the circuit board for enabling selective contact with the circuit board. Any and all electrical connections to the circuit board may be covered with a nonconductive insulating material or insulator after encapsulating the circuit board with the heat shrinkable plastic sleeve. In addition, prior to encapsulating the circuit board with the heat shrinkable plastic sleeve, a protective layer comprising a polyester film or plastic sheet may be used to cover the circuit board. This exemplary embodiment of the electrosurgery handpiece/pencil with smoke evacuation of the present invention supports use of the electrosurgery handpiece/pencil at high frequency ratings without insulation breakdown thereby providing a safer electrosurgery handpiece/pencil with smoke evacuation for use by surgeons.

The electrosurgery handpiece/pencil with smoke evacuation of the present invention may further include a cover member which covers the circuit board and the planar rectangular shaped platform near the top of the hollow tubular handpiece member and/or a swivel member that is connected to the second end of the hollow tubular handpiece member such that the electrical cord passes through it thereby enabling the electrical cord and any vacuum tube attached to the electrosurgery handpiece/pencil to twist or swivel freely thereby reducing drag or pulling down of the distal end of the electrosurgery handpiece/pencil when it is in use and being handled by a surgeon. The planar platform of the electrosurgery handpiece/pencil may include a recessed area for retaining the circuit board and the planar platform and the recessed area of the planar platform may both be rectangular in shape.

The planar platform of the electrosurgery handpiece/pencil may further include one or more channels for retaining one or more insulated wires that are connected to the circuit board. The electrosurgery handpiece/pencil may further comprise a nozzle member which retains the electrode and which fits inside an interior of the first end of the hollow tubular handpiece member. The nozzle member includes a first a first hollow tubular member, a second hollow tubular member having a smaller diameter than the first hollow tubular member, and a rib member that connects the first hollow tubular member to the second hollow tubular member in a manner such that the second hollow tubular member is positioned and located completely outside of the first hollow tubular member.

The second hollow tubular member may contain a slit along its length the facilitate seating and retention of an end of an electrode. The electrode is not obstructed in any way and can rotate to facilitate cutting and/or coagulation of tissue regardless of position or location. The electrode can also easily be removed and replaced with other types of electrodes. The rib member of the nozzle member may comprise a generally triangular shape having at least one rounded edge that conforms to the interior circumference of the hollow tubular handpiece member and that fits adjacent to the interior of the first end of the hollow tubular handpiece member. The rounded edge of the generally triangular shaped rib member has a length that is longer than the diameter of the second hollow tubular member of the nozzle member. The rib member of the nozzle member may also include a slot that is in communication with an interior of the second hollow tubular member and that retains a conductive member which is connected to the at least one wire of the electrosurgery handpiece/pencil that is connected to the circuit board. The electrode of the electrosurgery handpiece/pencil is seated within the second hollow tubular member of the nozzle member. The nozzle member described above assists in providing maximum smoke evacuation with minimal obstruction during cutting and/or coagulation using the electrosurgery handpiece/pencil with smoke evacuation of the present invention.

The electrosurgery handpiece/pencil of the present invention may also include a first opening that traverses through the planar platform and into the interior of the hollow tubular handpiece member that is located near the first end of the hollow tubular handpiece member to enable the at least one wire connecting the circuit board to the electrode to pass therethrough. The electrosurgery handpiece/pencil of the present invention may also include a second opening that traverses through the planar platform and into the interior of the hollow tubular handpiece member that is located near the second end of the hollow tubular handpiece member to enable the electrical cord containing one or more insulated wires for connecting the circuit board to an energy source to pass therethrough. The first and second openings in the planar platform of the electrosurgery handpiece/pencil of the present invention also assist in providing maximum smoke evacuation with minimal obstruction during cutting and/or coagulation using the electrosurgery handpiece/pencil of the present invention by limiting exposure of the electrical components and connections required for operating the electrosurgery handpiece/pencil to the interior of the hollow tubular handpiece member through which smoke and debris must pass during evacuation.

The one or more insulated wires that connect the circuit board to an energy source may include three insulated wires with one of the insulated wires being grounded. In addition, the one or more depressable button members on the electrosurgery handpiece/pencil with smoke evacuation of the present invention may include one depressable button for performing cutting and one depressable button for performing coagulation.

In another exemplary embodiment of the electrosurgery handpiece/pencil with smoke evacuation of the present invention, the electrosurgery handpiece/pencil with smoke evacuation includes a hollow tubular handpiece member having a first end and a second end, a planar platform located near a top of the hollow tubular handpiece member having a first opening into the hollow tubular handpiece member located near the first end of the hollow tubular handpiece member and a second opening into the interior of the hollow tubular handpiece member located near the second end of the hollow tubular handpiece member, an electrode positioned within the first end of the hollow tubular handpiece member, a circuit board seated on the planar platform, at least one wire traversing through the first opening that connects the circuit board to the electrode, an electrical cord containing one or more insulated wires traversing through the second opening which connects the circuit board to an energy source, and one or more depressable button members positioned above the circuit board for enabling selective contact with the circuit board. As previously explained above, this exemplary embodiment of the electrosurgery handpiece/pencil with smoke evacuation of the present invention assists in providing maximum smoke evacuation with minimal obstruction during cutting and/or coagulation using the electrosurgery handpiece/pencil of the present invention by limiting exposure of the electrical components and connections required for operating the electrosurgery handpiece/pencil to the interior of the hollow tubular handpiece member through which smoke and debris must pass during evacuation.

The nozzle member described above could also be included with this exemplary embodiment and would further assist in providing maximum smoke evacuation with minimal obstruction during cutting and/or coagulation due to the configuration of the nozzle. Further, encapsulating the circuit board with a heat shrinkable sleeve as described above could also be included with this exemplary embodiment to provide a safer instrument capable of use at high frequency ratings without insulation failure.

In yet another exemplary embodiment of the electrosurgery handpiece/pencil with smoke evacuation of the present invention, the electrosurgery handpiece/pencil with smoke evacuation includes a hollow tubular handpiece member having a first end and a second end, a planar platform located near a top of the hollow tubular handpiece member, a nozzle member connected to an interior of the first end of hollow tubular handpiece member where the nozzle member includes a first hollow tubular member, a second hollow tubular member having a smaller diameter than the first hollow tubular member, and a rib member connecting the first hollow tubular member to the second hollow tubular member such that the second hollow tubular member is positioned completely outside of the first hollow tubular member, an electrode positioned within the second hollow tubular member of the nozzle member, a circuit board seated on the planar platform, at least one wire for connecting the circuit board to the electrode, an electrical cord containing one or more insulated wires for connecting the circuit board to an energy source, and one or more depressable button members positioned above the circuit board for enabling selective contact with the circuit board.

The first and second openings in the planar platform described above that traverse through the planar platform and into the hollow tubular handpiece member could also be included with this exemplary embodiment and would further assist in providing maximum smoke evacuation with minimal obstruction during cutting and/or coagulation using the electrosurgery handpiece/pencil of the present invention by limiting exposure of the electrical components and connections required for operating the electrosurgery handpiece/pencil to the interior of the hollow tubular handpiece member through which smoke and debris must pass during evacuation. Further, encapsulating the circuit board with a heat shrinkable sleeve as described above could also be included with this exemplary embodiment to provide a safer instrument capable of use at high frequency ratings without insulation failure.

BRIEF DESCRIPTION OF THE DRAWINGS

The subject invention will hereinafter be described in conjunction with the appended drawing figures, wherein like numerals demote like elements.

FIG. 2 is a longitudinal cross-sectional view of the exemplary embodiment of the electrosurgery handpiece/pencil with smoke evacuation shown in FIG. 1;

FIG. 3 is a top open plan view of the exemplary embodiment of the electrosurgery handpiece/pencil with smoke evacuation shown in FIG. 1;

DETAILED DESCRIPTION OF EXEMPLARY EMBODIMENTS

Figure 1:
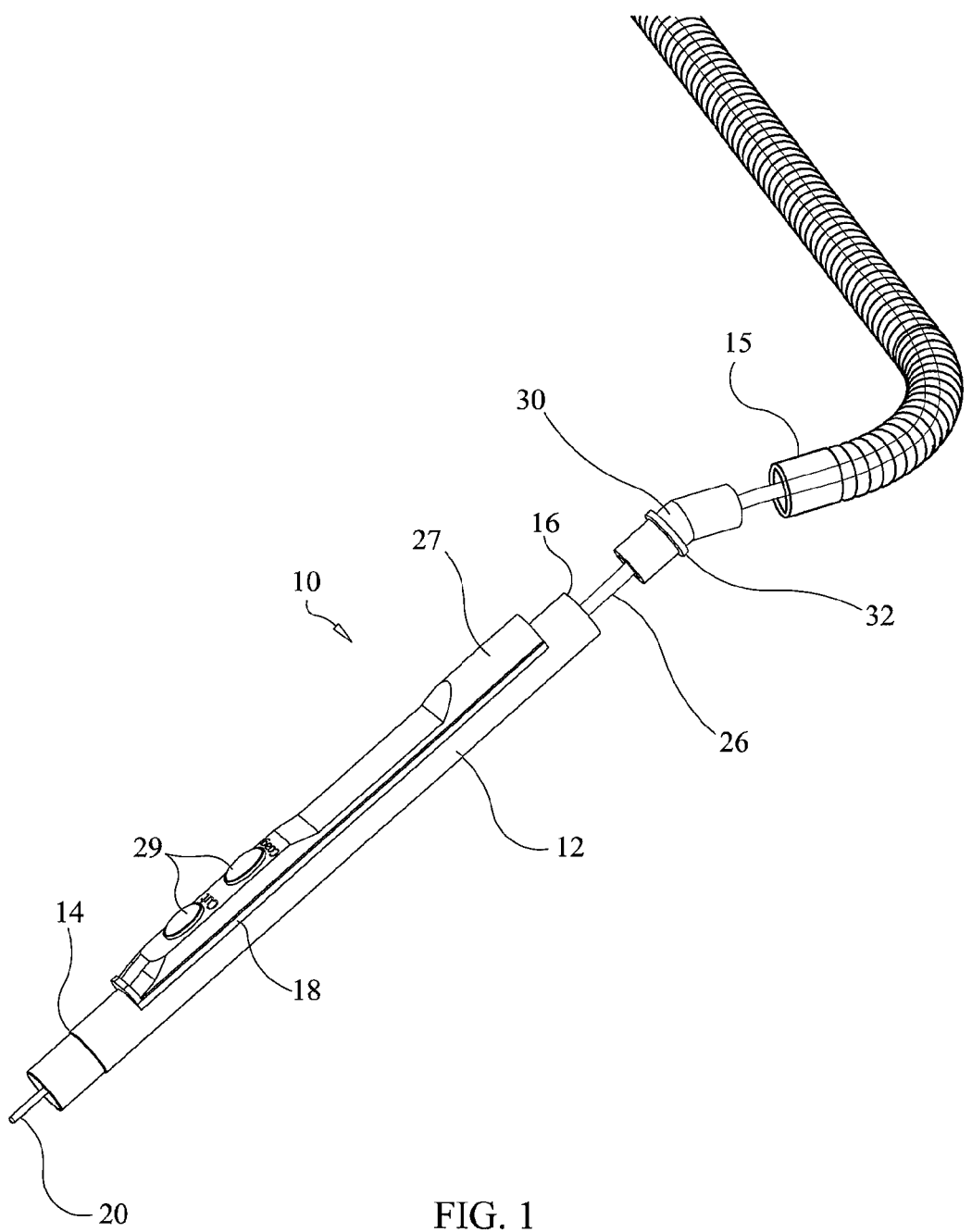
FIG. 1 is a perspective view of an exemplary embodiment of the electrosurgery handpiece/pencil with smoke evacuation of the present invention.

The electrosurgery handpiece/pencil with smoke evacuation of the present invention provides exemplary embodiments of an electrosurgery handpiece/pencil with smoke evacuation that enables use at high frequency ratings without insulation breakdown and that increases efficiency of smoke evacuation during cutting and/or coagulation. FIG. 1 shows a perspective view of an exemplary embodiment of the electrosurgery handpiece/pencil with smoke evacuation 10 of the present invention while FIGS. 2 and 3 show a longitudinal cross-sectional view of the exemplary embodiment of the electrosurgery handpiece/pencil with smoke evacuation 10 shown in FIG. 1 and a top open plan view of the exemplary embodiment of the electrosurgery handpiece/pencil with smoke evacuation 10 shown in FIG. 1, respectively. Electrosurgery handpiece/pencil 10 includes a hollow tubular handpiece member 12 having a first end 14 and a second end 16, a planar platform 18 located near a top of the hollow tubular handpiece member 12, an electrode 20 positioned within the first end 14 of the hollow tubular handpiece member 12, a circuit board 22 seated on the planar platform 18 where the circuit board 22 is contained within a heat shrinkable plastic sleeve 23 that has been heat shrunk to conform to the circuit board (See FIG. 14), at least one wire 24 for connecting the circuit board 22 to the electrode 20, an electrical cord 26 containing one or more insulated wires 28 for connecting the circuit board 22 to an energy source (not shown), and one or more depressable button members 29 positioned above the circuit board 22 for enabling selective contact with the circuit board 22. The one or more depressable button members 29 include a depressable button member for performing cutting with the electrosurgery handpiece/pencil with smoke evacuation 10 and a depressable button member for performing coagulation with the electrosurgery handpiece/pencil with smoke evacuation 10.

A vacuum tube 15 may be connected to the second end 16 of hollow tubular handpiece member 12 or alternatively, as shown in FIGS. 1-3, a vacuum tube 15 may be connected to a swivel member 30, which may comprise part of electrosurgery handpiece/pencil 10, where swivel member 30 is in turn connected to the second end 16 of hollow tubular handpiece member 12. Swivel member 30 may have a lip member 32 positioned about its circumference. Swivel member 30 is connected to the second end 16 of hollow tubular handpiece member 12 such that electrical cord 26 passes through it and into the vacuum tube 15 such that swivel member 30 is capable of swiveling or rotating about an inner or outer circumference of the hollow tubular handpiece member 12 near the second end 16 of the hollow tubular handpiece member 12. Electrosurgery handpiece/pencil 10 may further include a cover member 27 that covers the circuit board 22 and the planar platform 18. Cover member 27 may also retain depressable button members 29.

Electrosurgery handpiece/pencil with smoke evacuation 10 may also include an insulator 50 or an insulating material that covers an area of the circuit board 22 where one or more of the insulated wires 28 are connected to the circuit board 22. Further, the insulator or insulating material may be used to cover any and/or all connections to the circuit board 22 after encapsulating the circuit board 22 with the heat shrink sleeve 23. In addition, prior to encapsulating the circuit board with the heat shrink sleeve 23, a protective layer 76 (See FIG. 17), such as a polyester film or plastic sheet, may be used to cover the circuit board 22. Electrode 20 of the electrosurgery handpiece/pencil 10 may also include an insulation sleeve member 52 that covers at least a portion of the electrode 20.

Figure 4:
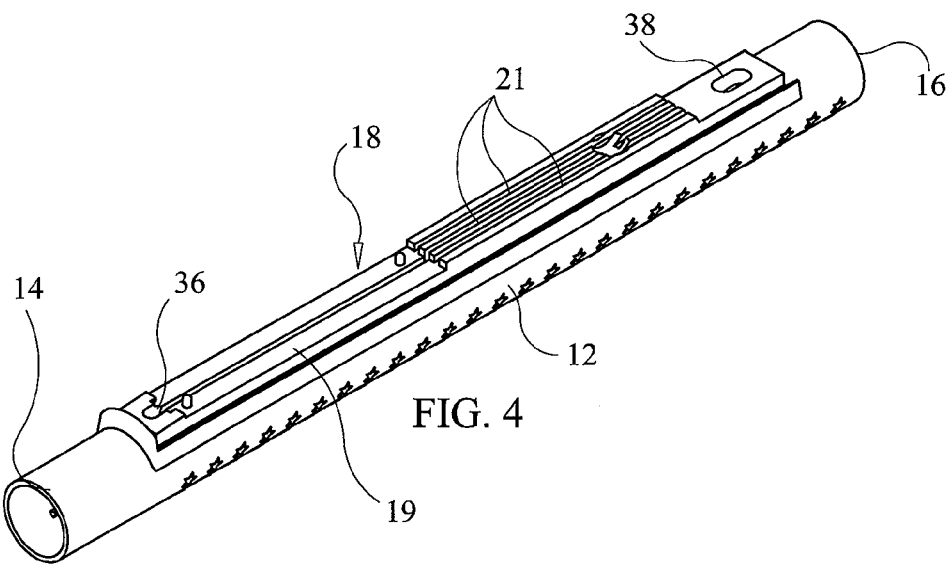
FIG. 4 is a perspective view of the hollow tubular handpiece member and planar platform of the exemplary embodiment of the electrosurgery handpiece/pencil with smoke evacuation shown in FIG. 1.

FIG. 4 is a perspective view of the hollow tubular handpiece member 12 and planar platform 18 of the exemplary embodiment of the electrosurgery handpiece/pencil with smoke evacuation 10 shown in FIG. 1. Planar member 18 may include a recessed area 19 which retains circuit board 22. Planar member 18 may also include one or more channels 21 for retaining one or more of the insulated wires 28 within the planar platform 18 before they are wrapped within the electrical cord 26 to enable connection of the circuit board 22 to an energy source (not shown). The one or more insulated wires 28 may include at least three insulated wires with one of the insulated wires being grounded and the other insulated wires being connected to portions of the circuit board that function to provide cutting and coagulation, respectively.

Planar member 18 includes a first opening 36 located near the first end 14 of hollow tubular handpiece member 12 that traverses through the planar platform 18 and into the interior of hollow tubular handpiece member 12 for enabling at least one wire 24, which connects the circuit board 22 to the electrode 20, to pass therethough. Planar member 18 also includes a second opening 38 located near the second end 16 of hollow tubular handpiece member 12 that traverses through the planar platform 18 and into the interior of hollow tubular handpiece member 12 for enabling the electrical cord 26, which contains one or more insulated wires 28 that connect the circuit board to an energy source, to pass therethrough. As shown in FIG. 4, planar platform 18 may be located on a top exterior surface of hollow tubular handpiece member 12 but it will be understood by those skilled in the art that different locations of the planar member in relation to the hollow tubular handpiece member are possible that will still result in providing increased efficiency for smoke evacuation when operating the electrosurgery handpiece/pencil 10. As further shown in FIG. 4, planar platform 18 may comprise a rectangular shape and recessed area 19 of planar platform 18 may also comprise a rectangular shape.

Figure 5:
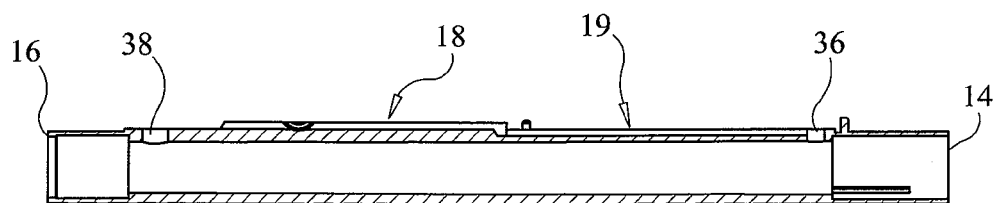
FIG. 5 is a longitudinal cross-sectional view of the hollow tubular handpiece member and planar platform of the exemplary embodiment of the electrosurgery handpiece/pencil with smoke evacuation shown in FIG. 4.

FIG. 5 is a longitudinal cross-sectional view of the hollow tubular handpiece member 12 and planar platform 18 of the exemplary embodiment of the electrosurgery handpiece/pencil with smoke evacuation 10 shown in FIG. 4. The recessed area 19 of planar member 18 on top of hollow tubular handpiece member 12 can be seen. First and second openings 36, 38 in planar member 18 that traverse the planar member 18 and the hollow tubular handpiece member 12 so that they access the interior of hollow tubular handpiece member 12 are also shown. A top plan view of the hollow tubular handpiece member 12 and planar platform 18 of the exemplary embodiment of the electrosurgery handpiece/pencil with smoke evacuation 10 shown in FIG. 4 is depicted in FIG. 5. Channels 21 in planar platform 18 previously described with reference to FIG. 4 are shown along with first and second openings 36, 38 in planar platform 18.

Figure 6:
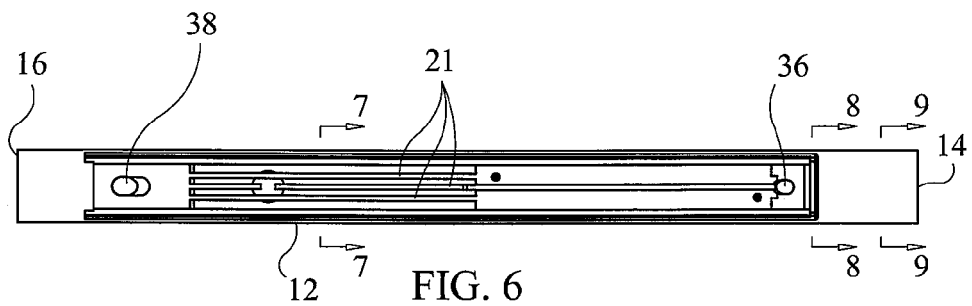
FIG. 6 is a top plan view of the hollow tubular handpiece member and planar platform of the exemplary embodiment of the electrosurgery handpiece/pencil with smoke evacuation shown in FIG. 4.
Figure 7:
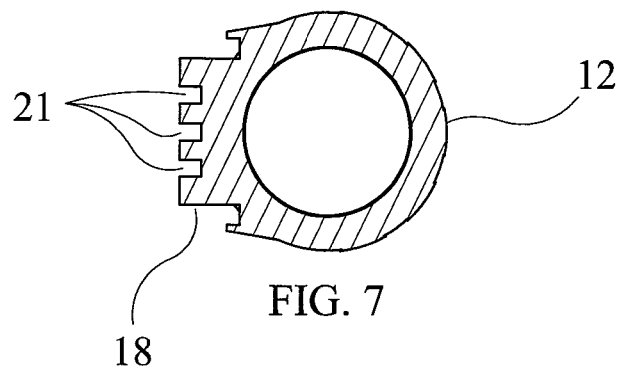
FIG. 7 is a cross-sectional view taken along line C-C of FIG. 6.
Figure 8:
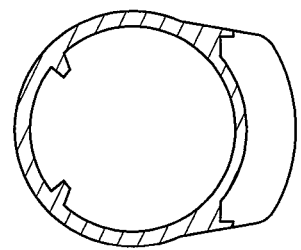
FIG. 8 is a cross-sectional view taken along line F-F of FIG. 6.
Figure 9:
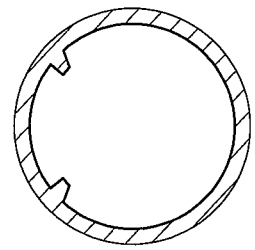
FIG. 9 is a cross-sectional view taken along line B-B of FIG. 6.

FIG. 7 is a cross-sectional view taken along line C-C of FIG. 6 and shows the channels 21 contained in the planar platform 18 located on top of hollow tubular handpiece member 12. Hollow tubular handpiece member 12 and planar platform 18, along with all of the other features described above with reference to planar platform 18 that may be included in planar platform 18, may be formed from a single molded piece. Cover member 27 shown in FIG. 1 may be separately formed, including by molding, and then positioned and tightly secured over the circuit board 22 and planar platform 18 once the circuit board 22 and its connections to other elements (such as wire member 24 and insulated wire members 28) have been properly made and positioned. Cover member 27 may be secured to planar platform 18 and/or hollow tubular handpiece member 12 by welding of thermoplastic materials. FIG. 8 is a cross-sectional view taken along line F-F of FIG. 6 and FIG. 9 is a cross-sectional view taken along line B-B of FIG. 6.

Figure 10:
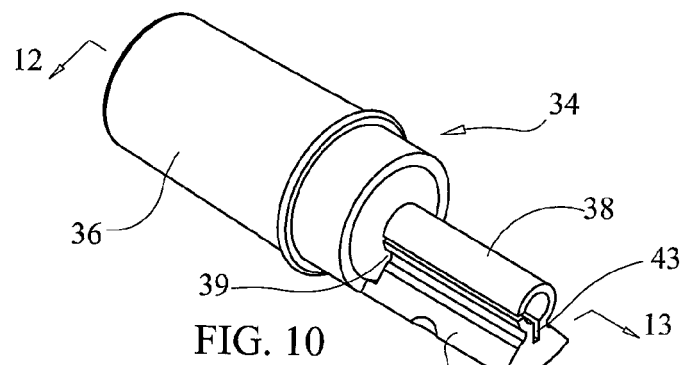
FIG. 10 is a perspective view of the nozzle member of the exemplary embodiment of the electrosurgery handpiece/pencil with smoke evacuation shown in FIG. 1.
Figure 11:
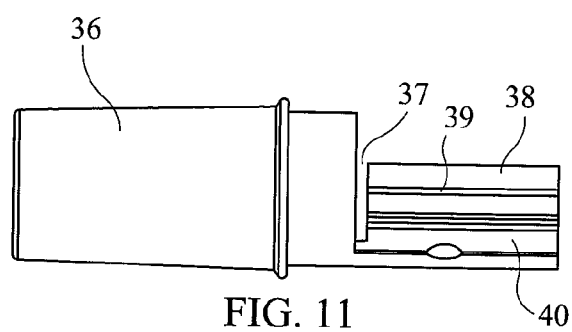
FIG. 11 is a side plan view of the nozzle member of the exemplary embodiment of the electrosurgery handpiece/pencil with smoke evacuation shown in FIG. 10.

A perspective view of the nozzle member 34 of the exemplary embodiment of the electrosurgery handpiece/pencil with smoke evacuation 10 shown in FIG. 1 is depicted in FIG. 10. Nozzle member 34 includes a first hollow tubular member 36, a second hollow tubular member 38 having a smaller diameter than the first hollow tubular member 36, and a rib member 40 connecting the first hollow tubular member 36 to the second hollow tubular member 38 such that the second hollow tubular member 38 is positioned/located completely outside of first hollow tubular member 36. Second hollow tubular member 38 of nozzle member 34 does not come in any contact with first hollow tubular member 36 of nozzle member 34 which can be better seen in FIG. 11. FIG. 11 is a side plan view of the nozzle member 34 of the exemplary embodiment of the electrosurgery handpiece/pencil 10 with smoke evacuation shown in FIG. 10 and clearly shows an empty space 37 between first hollow tubular member 36 and second hollow tubular member 38.

Figure 12:
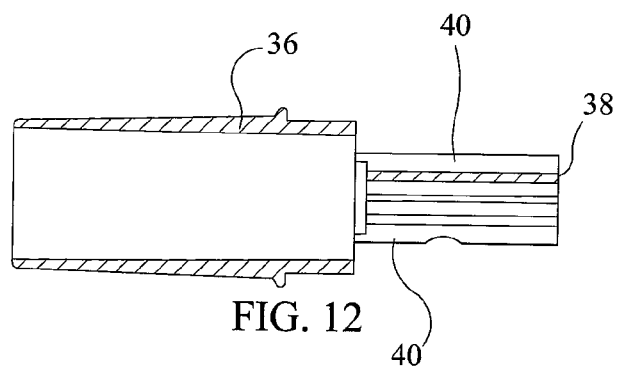
FIG. 12 is a cross-sectional view of the nozzle member of the exemplary embodiment of the electrosurgery handpiece/pencil with smoke evacuation of the present invention taken along line A-A of FIG. 11.
Figure 13:
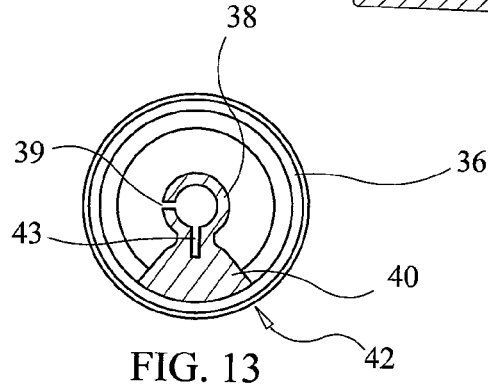
FIG. 13 is a cross-sectional view of the nozzle member of the exemplary embodiment of the electrosurgery handpiece/pencil with smoke evacuation of the present invention taken along line B-B of FIG. 11.

FIG. 12 is a cross-sectional view of the nozzle member 34 of the exemplary embodiment of the electrosurgery handpiece/pencil with smoke evacuation 10 of the present invention taken along line A-A of FIG. 11 and FIG. 13 is a cross-sectional view of the nozzle member 34 of the exemplary embodiment of the electrosurgery handpiece/pencil with smoke evacuation 10 of the present invention taken along line B-B of FIG. 11. As more clearly shown in FIGS. 10 and 13, second hollow tubular member 38 may include a slit 39 located along its length to facilitate seating and retention of the electrode 20. The rib member 40 of the nozzle member 34 may have a generally three dimensional rectangular shape having a rounded edge 42 that conforms to the interior circumference of the hollow tubular handpiece member 12 and that fits adjacent to the interior of the first end 14 of the hollow tubular handpiece member 12. As clearly shown in FIG. 13, the rounded edge 42 of the generally triangular shaped rib member 40 has a length that is longer than the diameter of the second hollow tubular member 38 of the nozzle member 34. The rib member 40 of the nozzle member 34 may also include a slot 43 that is in communication with an interior of the second hollow tubular member 38 and that retains a conductive member 44 (See FIG. 2) which is connected to the at least one wire 24 of the electrosurgery handpiece/pencil 10 that is connected to the circuit board 22. The electrode 20 of the electrosurgery handpiece/pencil 10 is seated within the second hollow tubular member 38 of the nozzle member 34.

Figure 14:
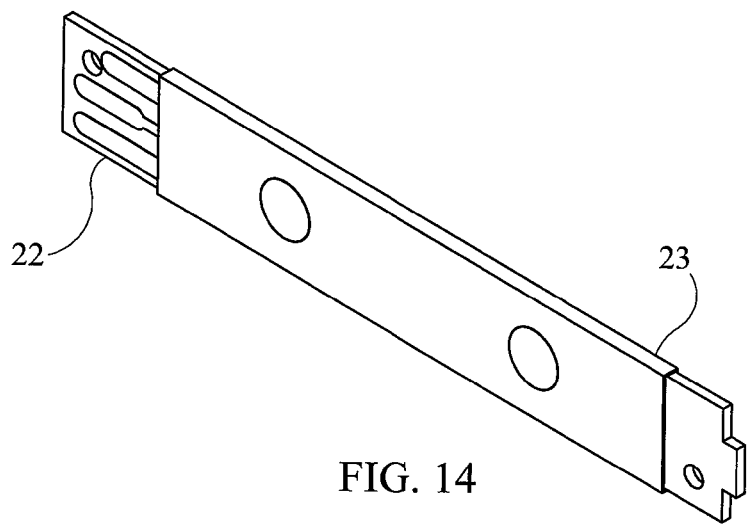
FIG. 14 is a perspective view of the circuit board of the exemplary embodiment of the electrosurgery handpiece/pencil with smoke evacuation of the present invention depicted in FIG. 1 shown with a heat shrinkable plastic sleeve that has been heat shrunk to conform to the circuit board.
Figure 15:
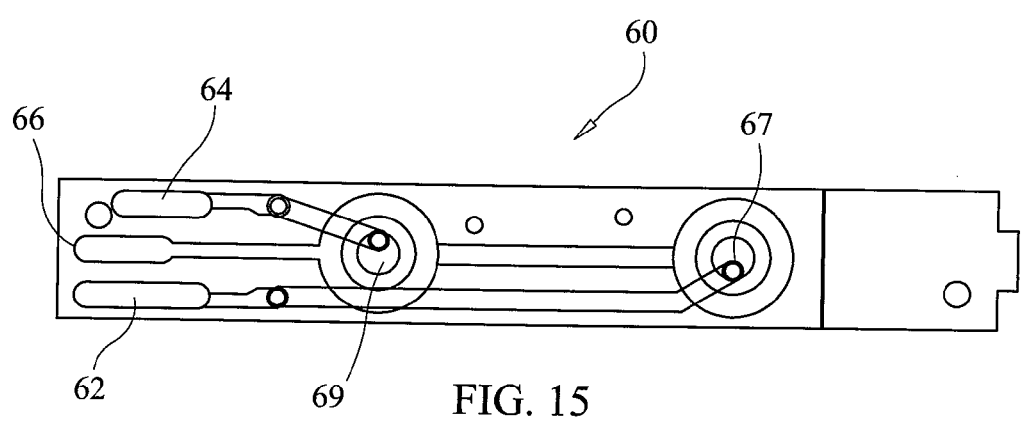
FIG. 15 is a plan view of the circuit contained on the circuit board of the exemplary embodiment of the electrosurgery handpiece/pencil with smoke evacuation of the present invention shown in FIG. 14.

FIG. 14 is a perspective view of the circuit board 22 of the exemplary embodiment of the electrosurgery handpiece/pencil with smoke evacuation 10 of the present invention depicted in FIG. 1 shown with a heat shrinkable plastic sleeve 23 that has been heat shrunk to conform to the circuit board 22. FIG. 15 is a plan view of the circuit 60 contained on the circuit board 22 of the exemplary embodiment of the electrosurgery handpiece/pencil with smoke evacuation 10 of the present invention shown in FIG. 14. As can be seen in FIG. 15, a first portion 62 of circuit 60 provides for cutting using the electrosurgery handpiece/pencil 10 of the present invention, a second portion 64 of the circuit 60 provides for coagulation using the electrosurgery handpiece/pencil 10 of the present invention, and a third portion 66 of the circuit 60 enables grounding.

Figure 16:
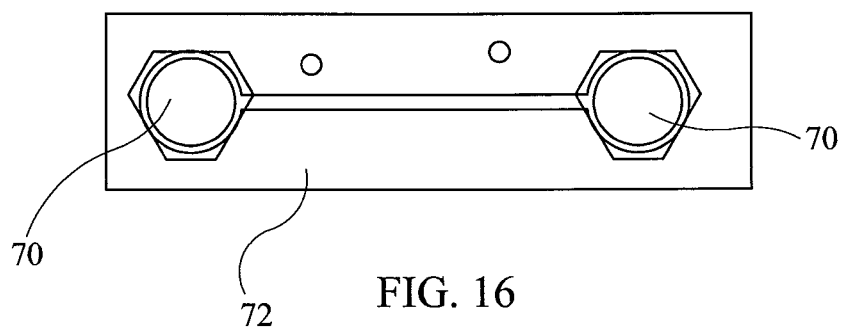
FIG. 16 is a top plan view of an area of the circuit board shown in FIG. 14 which shows the metal dome members and the spacer that are positioned over a portion of the circuit that correlates to the cutting and coagulation functions of the circuit.
Figure 17:
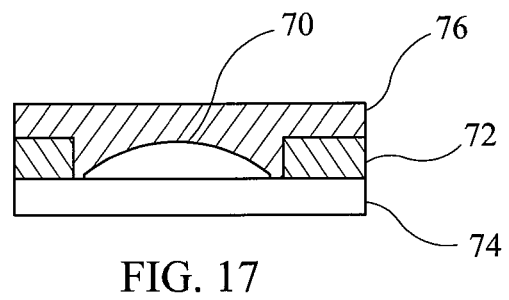
FIG. 17 is a cross-sectional view of a portion of the circuit board that includes one of the metal dome members prior to the circuit board being encapsulated with a heat shrinkable sleeve.

FIG. 16 is a top plan view of an area of the circuit board 22 shown in FIG. 14 which shows the metal dome members 70 and the spacer 72 that are positioned over a portion of the circuit 60 that correlates to the cutting and coagulation functions of the circuit 60. FIG. 17 is a cross-sectional view of a portion of the circuit board 22 that includes one of the metal dome members 70 prior to the circuit board being encapsulated with a heat shrinkable sleeve 23. The circuit 60 is printed onto the substrate 74 which may comprise a laminate, for example. Metal dome members 70 are positioned over metal circles 67, 69 of circuit 60 (See FIG. 15) that correspond to cutting and coagulation, respectively. Spacer 72 is positioned over the parts of the circuit 60 that surround the metal circles 67, 69 and then a protective layer 76 comprising a polyester film or plastic sheet, for example, is positioned over the metal dome members 70 and spacer 72. A heat shrink sleeve 23 is then positioned over this combination of materials on the circuit board 22 and a heat source is then used to heat the heat shrink sleeve 23 until it shrinks to fit the circuit board 22.

The exemplary embodiment of the electrosurgery handpiece/pencil with smoke evacuation 10 of the present invention shown and described with reference to FIGS. 1-17 enables use of the electrosurgery handpiece/pencil 10 at high frequency ratings without insulation breakdown and provides for increased efficiency of smoke evacuation during cutting and/or coagulation. Covering the circuit board with a heat shrinkable plastic sleeve and heating the heat shrinkable plastic sleeve until it conforms to the circuit board enables use of the electrosurgery handpiece/pencil at high frequencies without insulation breakdown. Further covering any and/or all electrical connections to the circuit board with a nonconductive insulating material or insulator after encapsulating the circuit board with the heat shrinkable plastic sleeve further supports use of the electrosurgery handpiece/pencil at high frequencies without insulation breakdown. In addition, further covering the circuit board with a protective layer, such as a polyester film or plastic sheet, for example, prior to encapsulating the circuit board with the heat shrinkable plastic sleeve, further supports the use of the electrosurgery handpiece/pencil at high frequencies without insulation breakdown. Including the nozzle member described above in the electrosurgery handpiece/pencil 10 assists in providing increased efficiency of smoke evacuation with minimal obstruction during cutting and/or coagulation using the electrosurgery handpiece/pencil with smoke evacuation 10. Further providing first and second openings in the planar platform of the electrosurgery handpiece/pencil 10 of the present invention at certain locations on the planar platform also assists in providing increased efficiency of smoke evacuation with minimal obstruction during cutting and/or coagulation using the electrosurgery handpiece/pencil of the present invention by limiting exposure of the electrical components and connections required for operating the electrosurgery handpiece/pencil to the interior of the hollow tubular handpiece member through which smoke and debris must pass during evacuation. Accordingly, since different features/elements of the electrosurgery handpiece/pencil with smoke evacuation 10 support different improvements to the electrosurgery handpiece/pencil, it will be understood by those skilled in the art that additional exemplary embodiments of the invention may include just one or more of the different features/elements described above that support the improvements.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An electrosurgery pencil comprising:
   a hollow tubular handpiece member having a first end and a second end;
   a planar platform having a recessed area located near a top of the hollow tubular handpiece member;
   an electrode positioned within the first end of the hollow tubular handpiece member;
   a circuit board seated within the recessed area of said planar platform wherein said circuit board is contained within a heat shrinkable plastic sleeve that has been heat shrunk to conform to the circuit board;
   at least one wire for connecting the circuit board to the electrode;
   an electrical cord containing one or more insulated wires for connecting said circuit board to an energy source; and
   one or more depressable button members positioned above said circuit board for enabling selective contact with said circuit board.

2. The electrosurgery pencil of claim 1 further comprising a cover member that covers the circuit board and the planar platform.

3. The electrosurgery pencil of claim 1 further comprising a swivel member connected to the second end of the hollow tubular member such that the electrical cord passes therethrough.

4. The electrosurgery pencil of claim 1 wherein said planar platform comprises a rectangular shape and said recessed area of the planar platform comprises a rectangular shape.

5. The electrosurgery pencil of claim 1 wherein the planar platform comprises one or more channels for retaining said one or more insulated wires within the planar platform.

6. The electrosurgery pencil of claim 1 further comprising a nozzle member for retaining said electrode which fits within an interior of the first end of the hollow tubular handpiece member, said nozzle member having a first hollow tubular member, a second hollow tubular member having a smaller diameter than said first hollow tubular member, and a rib member connecting the first hollow tubular member to the second hollow tubular member such that said second hollow tubular member is positioned completely outside of said first hollow tubular member.

7. The electrosurgery pencil of claim 6 wherein said second hollow tubular member has a slit located along its length.

8. The electrosurgery pencil of claim 6 wherein said rib member comprises a generally triangular shape having a rounded edge that fits adjacent to the interior of the first end of the hollow tubular handpiece member and that is longer than a diameter of said second hollow tubular member.

9. The electrosurgery pencil of claim 6 wherein the rib member includes a slot which is in communication with a interior of said second hollow tubular member and which retains a conductive member that is connected to said at least one wire that is connected to the circuit board.

10. The electrosurgery pencil of claim 9 wherein the electrode is seated within said second hollow tubular member.

11. The electrosurgery pencil of claim 1 further comprising a first opening traversing through said planar platform and into an interior of said hollow tubular handpiece member wherein said first opening is located near the first end of the hollow tubular handpiece member fur enabling said at least one wire to pass therethrough.

12. The electrosurgery pencil of claim 11 further comprising a second opening traversing through said planar platform and into the interior of said hollow tubular handpiece member wherein said second opening is located near the second end of the hollow tubular handpiece member for enabling said electrical cord to pass therethrough.

13. The electrosurgery pencil of claim 1 further comprising a separate insulator that covers an area of said circuit board where said one or more insulated wires are connected to the circuit board.

14. The electrosurgery pencil of claim 1 wherein said one or more insulated wires comprises at least three insulated wires where one of the insulated wires is grounded.

15. The electrosurgery pencil of claim 1 wherein said one or more depressable button members comprise a depressable button member for performing cutting and a depressable button member for performing coagulation.

16. The electrosurgery pencil of claim 1 further comprising a protective layer that covers a top of the circuit board and that is positioned between the circuit board and the heat shrinkable plastic sleeve.

17. An electrosurgery pencil comprising:
a hollow tubular handpiece member having a first end and a second end;
a planar platform located near a top of the hollow tubular handpiece member, the planar platform having a first opening therethrough which extends into an interior of the hollow tubular handpiece member located near the first end of the hollow tubular handpiece member and a second opening therethrough which extends into the interior of the hollow tubular handpiece member located near the second end of the hollow tubular handpiece member;
an electrode positioned within the first end of the hollow tubular handpiece member;
a circuit board seated on said planar platform;
at least one wire traversing through the first opening which connects the circuit board to the electrode;
an electrical cord containing one or more insulated wires traversing through the second opening which connects the circuit board to an energy source; and
one or more depressable button members positioned above the circuit board for enabling selective contact with the circuit board.

18. The electrosurgery pencil of claim 17 wherein said circuit board is contained within a heat shrinkable plastic sleeve that has been heat shrunk to conform to the circuit board.

19. The electrosurgery pencil of claim 18 wherein a top of the circuit board is covered with a protective layer located between the circuit board and the heat shrinkable plastic sleeve and wherein all electrical connections to the circuit board are covered with a separate nonconductive insulating material.

20. An electrosurgery pencil comprising:
a hollow tubular handpiece member having a first end and a second end;
a planar platform located near a top of the hollow tubular handpiece member;
a nozzle member connected to an interior of the first end of the hollow tubular handpiece member, said nozzle member having a first hollow tubular member, a second hollow tubular member having a smaller diameter than said first hollow tubular member, and a rib member connecting the first hollow tubular member to the second hollow tubular member such that said second hollow tubular member is positioned completely outside of said first hollow tubular member and said second hollow tubular member is located closer to the first end of the hollow tubular handpiece member than the first hollow tubular member;
an electrode positioned within only said second hollow tubular member of said nozzle member;
a circuit board seated on said planar platform;
at least one wire for connecting the circuit board to the electrode;
an electrical cord containing one or more insulated wires for connecting said circuit board to an energy source; and
one or more depressable button members positioned above said circuit board for enabling selective contact with said circuit board.

21. The electrosurgery pencil of claim 20 further comprising a first opening traversing through said planar platform and into an interior of said hollow tubular handpiece member wherein said first opening is located near the first end of the hollow tubular handpiece member for enabling said at least one wire to pass therethrough and a second opening traversing through said planar platform and into the interior of said hollow tubular handpiece member wherein said second opening is located near the second end of the hollow tubular handpiece member for enabling said electrical cord to pass therethrough.

22. The electrosurgery pencil of claim 20 wherein said circuit board is contained within a heat shrinkable plastic sleeve that has been heat shrunk to conform to the circuit board.

23. The electrosurgery pencil of claim 22 wherein a top of the circuit board is covered with a protective layer located between the circuit board and the heat shrinkable plastic sleeve and wherein all electrical connections to the circuit board are covered with a separate non-conductive insulating material.

* * * * *